United States Patent
Caspary (10) Patent No.: US 12,296,093 B2
(45) Date of Patent: May 13, 2025

(54) FAN HAVING DAMPING AND SEALING ELEMENTS BETWEEN VARIOUS HOUSING PARTS

(71) Applicant: Drägerwerk AG & Co. KGaA, Lübeck (DE)

(72) Inventor: René-Christian Caspary, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 306 days.

(21) Appl. No.: 17/923,001

(22) PCT Filed: Mar. 5, 2021

(86) PCT No.: PCT/EP2021/055567
§ 371 (c)(1),
(2) Date: Nov. 3, 2022

(87) PCT Pub. No.: WO2021/223923
PCT Pub. Date: Nov. 11, 2021

(65) Prior Publication Data
US 2023/0173204 A1    Jun. 8, 2023

(30) Foreign Application Priority Data

May 5, 2020 (DE) .......................... 102020002671.0

(51) Int. Cl.
*A61M 16/00* (2006.01)
*A61M 16/20* (2006.01)
(Continued)

(52) U.S. Cl.
CPC ...... *A61M 16/0066* (2013.01); *A61M 16/208* (2013.01); *F04D 27/008* (2013.01);
(Continued)

(58) Field of Classification Search
CPC ............ F04D 29/4213; F04D 29/4226; F04D 29/603; F04D 29/668; A61M 16/0066; A61M 2205/42
See application file for complete search history.

(56) References Cited

U.S. PATENT DOCUMENTS 5,875,783 A    3/1999    Kullik
6,474,960 B1   11/2002   Hansmann
(Continued)

FOREIGN PATENT DOCUMENTS

CN    205383109 U    7/2016
DE    197769 C       4/1908
(Continued)

*Primary Examiner* — Sabbir Hasan
(74) *Attorney, Agent, or Firm* — McGlew and Tuttle, P.C.

(57) ABSTRACT

A compressor (1), or ventilator/anesthesia device with the compressor, includes a housing, a rotatable impeller (6) connected via a drive shaft (4) to an electric motor (5) to deliver gas from an inlet (8), upstream on a suction side (7) through a flow duct (11) to a downstream outlet (10) on a delivery side (9). The compressor impeller is partially enclosed by the housing, as a collection housing (2) on the delivery side, and a cover element (12), on the suction side separated in sections from the compressor impeller by a gap (13). An uncoupling element (15) is arranged, for vibration damping and for at least partial sealing of the housing interior against a surrounding area (16), between the cover element and the collection housing and between a functional component (14) connected at least indirectly to the compressor impeller and/or to the electric motor and the collection housing.

20 Claims, 4 Drawing Sheets

(51) Int. Cl.
*F04D 27/00* (2006.01)
*F04D 29/08* (2006.01)
*F04D 29/16* (2006.01)
*F04D 29/42* (2006.01)
*F04D 29/66* (2006.01)

(52) U.S. Cl.
CPC ......... *F04D 29/083* (2013.01); *F04D 29/162* (2013.01); *F04D 29/4213* (2013.01); *F04D 29/4226* (2013.01); *F04D 29/663* (2013.01); *F04D 29/668* (2013.01); *A61M 2205/42* (2013.01)

(56) References Cited

U.S. PATENT DOCUMENTS

| | | |
|---|---|---|
| 2014/0069432 A1 | 3/2014 | Mebasser et al. |
| 2014/0127049 A1 | 5/2014 | Yoneda et al. |
| 2014/0325789 A1 | 11/2014 | Hill et al. |
| 2018/0064894 A1 | 3/2018 | Fu et al. |
| 2019/0038866 A1 | 2/2019 | Chalvignac et al. |

FOREIGN PATENT DOCUMENTS

| | | |
|---|---|---|
| DE | 19714644 A1 | 10/1998 |
| DE | 19715581 C1 | 2/1999 |
| DE | 19904119 C2 | 6/2002 |
| DE | 10225092 A1 | 2/2003 |
| DE | 102015116350 A1 | 3/2017 |
| WO | 2007134405 A1 | 11/2007 |
| WO | 2019235422 A1 | 12/2019 |

FAN HAVING DAMPING AND SEALING ELEMENTS BETWEEN VARIOUS HOUSING PARTS

CROSS REFERENCE TO RELATED APPLICATIONS

This application is a United States National Phase Application of International Application PCT/EP2021/055567, filed Mar. 5, 2021, and claims the benefit of priority under 35 U.S.C. § 119 of German Application DE 102020002671.0, filed May 5, 2020, the entire contents of which are incorporated herein by reference.

TECHNICAL FIELD

The present invention pertains to a compressor for delivering an air and/or gas stream with a housing, in the housing interior of which a rotatably mounted compressor impeller connected to an electric motor via a drive shaft is arranged. During a rotation of the compressor impeller, the air and/or gas stream is delivered from an inlet arranged upstream of a suction side of the compressor impeller through a flow duct to an outlet arranged downstream on a delivery side of the compressor impeller. Compressors of this class are used, e.g., in ventilators or anesthesia devices in order to supply a patient with the respective needed breathing gas stream.

TECHNICAL BACKGROUND

Ventilators or anesthesia devices are often supplied with the respective gas mixture needed via the central gas supply system of a hospital, to which the devices are connected. However, blowers with suitable compressors, by which a breathing gas stream, which may contain air or a gas mixture having a different composition, is delivered with the necessary status parameters to the patient, are increasingly installed in ventilators and anesthesia devices. It is equally conceivable in this connection that the breathing gas stream is delivered at a continuous pressure level or the pressure level is varied dynamically in order thus to achieve, e.g., specific ventilation modes or ventilation maneuvers.

It is essential for the blowers used in ventilators or anesthesia devices that these have a compact construction, be able to generate a breathing gas stream that has the status parameters necessary for the ventilation of the particular patient and to emit as little sound as possible, which is often elicited in the form of structure-borne noise due to vibrations of motor or blower parts. Since it is usually impossible to meet all three configuration criteria mentioned above to an equal extent, the development and configuration of the compressors of this class is often based on an optimization, so that each of the three configuration criteria are met at least sufficiently.

A blower of this class with a rotary compressor for a ventilation system is known in this connection from U.S. Pat. No. 5,875,783. Because of the specific dimensioning and shaping as well as of the properties achieved hereby, the compressor described is especially suitable for following pressure fluctuations, which occur above all during the assisting of a patient breathing at least partially spontaneously.

Another blower for ventilators and anesthesia devices is known from DE 197 14 644 C2. The blower has a radial compressor with backward curved blades. Because of the special shape of the compressor impeller, it is possible to cover a broad range of speeds and pressures within a time period of only a few milliseconds in case of a corresponding actuation of the electric motor.

Further, WO 2007/134405 A1 describes a blower which is said to be characterized by low sound emissions. It is essential for the blower described that a plurality of compressor stages are arranged in series in terms of flow and all flow-carrying components are enclosed by an additional housing.

Another rotary compressor is known from DE 199 04 119 C2. The compressor is driven by an electronically commuted d.c. motor, whose rotor is formed by a permanent magnet connected to the compressor impeller, the rotor being hermetically separated from the stator of the d.c. motor by a slit pot. Furthermore, the compressor impeller is mounted by means of an aerodynamic gas slide bearing and is enclosed by a housing composed of a plurality of components. The direct contact, in particular, between rotating parts of the electric motor and the housing shall be prevented by means of the technical solution described.

Since the solution described in DE 199 04 119 C2 has a comparatively complicated configuration, prior-art solutions that represent an alternative to this provide for an additional housing, the so-called secondary housing, which encloses the compressor as well as the spiral housing, also called primary housing, which adjoins said compressor and guides the air or gas stream.

In order to achieve a further minimization of the sound emission with the use of a secondary housing, actions are often taken to reduce vibration transmissions. It is known, for example, in this connection to mount the assembly unit comprising the motor, the compressor impeller and the primary housing by means of flexible, soft mounts or uncoupling elements in the secondary housing. Soundproofing is achieved in this case by an additional housing and additional insulating elements, so that even though the noise burden for a patient and the nursing staff is ultimately minimized, it is made impossible to obtain a compact compressor configuration.

It is problematic in the case of the compressors known from the state of the art, especially those used in ventilators and anesthesia devices, that even though it is possible to configure them in respect to the necessary performance parameters, a compact configuration and low sound emissions do, however, additionally represent essential configuration criteria. Meeting all these three configuration criteria as optimally as possible usually represents a considerable problem.

SUMMARY

Based on the compressors known from the state of the art and the above-described problems, a basic object of the present invention is to propose a technical solution that makes it possible to provide a compressor optimized in respect to the three essential configuration criteria, namely, the performance characteristic, construction and sound emission. A compressor shall thus be provided that is suitable for use in a ventilator and/or anesthesia device and is characterized by a comparatively compact configuration, by suitable performance characteristics as well as by low sound emissions. It is highly significant in this connection that the burdens of a patient as well as of the nursing staff due to sound emissions, which originate from the compressor and are caused, e.g., by vibrations of different components, shall be at least minimized. It should be borne in mind in relation to the pneumatic performance characteristics for the solution to be proposed that the compressor shall be able to be used for ventilating patients, and specific ventilation parameters shall be able to be obtained depending on the particular disease of a patient. Moreover, such a compressor should be characterized by a comparatively simple structural configuration, which can be obtained by means of prior-art construction principles, as well as by the lowest manufacturing costs possible. Furthermore, it is desirable for a compressor based on the present invention to cause the lowest possible flow losses during the carrying of air or gas, at least in operating ranges that are frequently used, and to have a maintenance-friendly configuration.

The above-described object is accomplished with a blower as well as with a ventilator or anesthesia device as described. Advantageous embodiments of the present invention are disclosed and will be explained in more detail in the following description partly in reference to the figures.

The present invention pertains to a compressor for delivering an air and/or gas stream with a housing, in the housing interior of which a rotatably mounted compressor impeller connected to an electric motor via a drive shaft is arranged, during the rotation of which the air and/or gas stream is delivered from an inlet arranged upstream on a suction side of the compressor impeller through a flow duct to an outlet arranged downstream on a delivery side of the compressor impeller. A compressor characterized according to the present invention is characterized in that the compressor impeller arranged in the housing interior is enclosed, on the one hand, at least in some areas, by the housing, which represents a collection housing for the air and/or gas stream displaced radially to the outside and which preferably has a spiral configuration and is arranged at least partially on the delivery side of the compressor impeller, and, on the other hand, by a cover element, which is arranged at least partially on the suction side of the compressor impeller and is separated in at least some sections by a gap from the compressor impeller. At least one respective uncoupling element is arranged in this case, on the one hand, between the cover element and the collection housing and, on the other hand, between a functional component connected at least indirectly to the compressor impeller and the collection housing for vibration damping and for an at least partial sealing of the housing interior against a surrounding area.

It is essential for the solution according to the present invention that the housing interior, which is filled with the air or gas stream to be delivered at least from time to time, and in which the rotatably mounted compressor impeller is arranged, is enclosed in at least some areas by a housing, which has at least two components, namely, a preferably spirally configured collection housing, i.e., a so-called spiral housing, as well as a cover element, wherein at least one uncoupling element is provided for vibration damping and for an at least partial sealing of the housing interior against a surrounding area both between the collection housing and the cover element and between the collection housing and a functional component, which adjoins this and which is connected at least indirectly to the electric motor and/or to the compressor impeller. The preferably spirally configured collection housing is thus uncoupled in terms of vibrations from both the functional component and the cover element, which is arranged upstream on the suction side of the compressor impeller, so that a damping of occurring vibrations is achieved, for example, by the use of an elastic uncoupling element. Transmission of vibrations from the cover element to the spiral housing but also from the adjoining functional component to the spiral housing is thus reliably prevented or at least minimized. The collection housing defining the housing interior at least in some areas is uncoupled in this manner especially from the electric motor and from the compressor impeller connected to it at least indirectly in respect to a possible vibration transmission and thus consequently guarantees a reduction of the emitted sound emissions, without an additional secondary housing, which encloses the collection housing, which latter defines the housing interior at least in some areas and which can also be called primary housing, having to be provided for this purpose. The transmission of vibrations, which are generated by the electric motor and/or by the compressor impeller and which are emitted by a functional component, especially by a housing part, is effectively and markedly reduced by the selected uncoupling. The collection housing itself does not act, above all, as an emission surface, because it is uncoupled from the vibration source and is even a part of an encapsulation of the compressor according to the technical solution according to the present invention. The collection housing assumes here as a primary housing the same function as the so-called secondary housing in the solutions known from the state of the art. It is thus essential for the present invention that the collection housing is indirectly fastened via suitable uncoupling elements, which prevent or at least minimize the transmission of vibrations, to adjoining components, which may be induced to perform vibrations during the operation of the compressor.

It is possible, on the one hand, due to the provision of a split housing for the compressor impeller in combination with flexible elements, which at the same time seal the housing interior against the surrounding area, between the housing parts, i.e., between the cover element and the collection housing and/or between the collection housing and an adjoining functional component, to prevent the transmission of vibrations, which originate from the compressor impeller and/or from the electric motor, to the collection housing, and, on the other hand, to nevertheless minimize gap losses in the housing interior between the suction side and the delivery side. This is achieved according to the present invention by arranging on the suction side of the compressor impeller a cover element, which is separated from the collection housing by an uncoupling element, and which is separated from the rotatably mounted compressor impeller by a comparatively narrow gap only. Since the cover element provided according to the present invention is not connected, unlike as is known in the state of the art, via a flexible suspension to the electric motor, which has itself a rigid connection via the drive shaft to the compressor impeller, comparatively narrow tolerances can be ensured when the present invention is embodied. The housing of the housing interior with the compressor impeller mounted rotatably therein is enclosed according to the present invention by a housing, which has as its components a cover element as well as a collection housing, which is preferably configured as a spiral housing. The functional component, which adjoins the collection housing and is connected via a coupling element, is preferably a part of a collection housing and/or of an encapsulation of the electric motor, which drives the compressor impeller. It is likewise conceivable that the functional component is connected at least indirectly or directly to the electric motor. A transmission of vibrations, which are generated at least from time to time during the operation by the electric motor with its moving components, especially by the drive shaft with the compressor impeller fastened to it, is reliably prevented or at least reduced by the elastic uncoupling element between the preferably spirally configured collection housing and the functional component. The functional component preferably has a sealing surface with a circular or oval configuration, at which the uncoupling element, which establishes an elastic, at least partially flexible connection between the functional component and the collection housing. The uncoupling element is used here both to prevent or at least minimize a transmission of vibrations as well as to seal the housing interior, in which the at least partially compressed air or gas stream being delivered by the compressor impeller is located, against the surrounding area.

In a special embodiment of the present invention, the cover element, which is arranged on the suction side of the compressor impeller, is configured in the form of a disk. The disk has here, in the interior of the disk, a passage, which preferably has a circular disk-shaped cross section and through which the air and/or gas stream drawn in based on the rotation of the compressor impeller enters into the inlet of the compressor.

According to a special variant of the present invention, the cover element is connected in at least some areas indirectly or directly to a flow guide unit, which has at least one guide element, e.g., in the form of a guide blade, for guiding the air and/or gas stream discharged on the delivery side of the compressor impeller. It is advantageous if the cover element is supported via the flow guide unit, and it is conceivable in this connection that the cover element is connected on a side of the flow guide element, which side is located opposite the gap between the cover element and the compressor impeller, to the uncoupling element arranged between the spiral housing and the functional component. It is ensured in this case by the uncoupling element that vibrations, which may be generated during the flow through the flow guide element, will not be transmitted to the collection housing, as a result of which sound emissions, which are generated by the emission of structure-borne noise from the collection housing, are in turn reliably prevented from being generated or are at least minimized.

According to a special embodiment, the flow guide unit has a ring-shaped configuration and has a plurality of guide blades (vanes) arranged along a ring-shaped circumferential surface. The compressor impeller is arranged here in the interior of the flow guide unit and is mounted rotatably such that the air and/or gas stream discharged from the compressor impeller on the delivery side at least from time to time during the operation impacts on the plurality of guide blades at least partially. The stationary guide blades do not preferably adjoin the compressor impeller rotating during the operation directly, and configuring the area between the compressor impeller and the guide blades in the form of a diffuser presents itself as an advantageous solution. The diffusor is preferably configured depending on the flow parameters, which occur in at least one operating point or operating range, which occurs comparatively frequently during the operation of the compressor.

It is, furthermore, advantageous if the compressor impeller has main blades extending in the radial direction from the outer circumference of the compressor impeller at least nearly at right angles over at least a large part of an entire cross section of the flow duct as well as at least two respective intermediate blades, which are arranged between the main blades and have a shorter configuration than the main blades. Both the main blades and the intermediate blades have such a, for example, bent and/or curved configuration that the air and/or gas stream to be delivered is compressed as effectively as possible and that, above all, flow losses are minimized.

A compressor impeller configured as described above is characterized, in addition to a special effectiveness during the compression of air and/or gas, above all by comparatively low sound emissions, because swirling is reliably avoided in the interior of the compressor impeller based on the specially configured main and intermediate blades. It is also ensured with a compressor impeller having such a configuration, comprising a main blade and intermediate blades, that a high pneumatic performance can be achieved despite a comparatively small space available for installation.

A compressor impeller, which has an external diameter of 29 mm to 34 mm and preferably 30 mm to 32 mm, is used according to an especially advantageous variant of the present invention. Preferably 8 to 10, especially 9 to 13 main blades are provided on a compressor impeller, and at least two respective intermediate blades each are arranged between them. The intermediate blades extend each from the outer circumference of the compressor impeller in the direction of the center, but they are shorter than the main blades and are preferably likewise curved and/or bent. In a very special embodiment, the intermediate blades arranged between the main blades have different lengths in the radial direction, have an unequal profile and/or have blade areas of different sizes. Thus, at least two intermediate blades, which have correspondingly different configurations, are arranged between two preferably ring-shaped main blades according to this special embodiment.

In another embodiment, at least one inlet muffler is arranged upstream of the compressor impeller. The inlet muffler preferably has at least one spiral muffler. The flow cross section, which arises from the distance between the turns of the spiral and the spiral height, should advantageously preferably be greater by about 25-35% and preferably by about 30% than the inlet cross section of the compressor impeller. It is, in general, advantageous if the distance between the individual turns of the spiral is kept short in order thus to minimize sound emissions, which are caused by flow noises and can be released via the inlet. A reduction of the distance of the spiral walls does, however, lead, in case of a defined flow cross section to an increase in the resulting overall height of the spiral of a spiral muffler. In order, however, to make it nevertheless possible to obtain a compact and possibly flat configuration, the inlet muffler has, according to a special variant of the present invention, a spiral muffler with at least two separate spiral elements arranged at least partially one in the other. It is conceivable in this connection that the spirals interlaced in one another have the same flow cross sections or different flow cross sections. The distance of the spiral walls is, however, preferably reduced by half in case of the use of a second spiral, which leads to a marked improvement of the muffling characteristic of a spiral muffler at equal or at least similar external dimensions.

An inlet muffler, in which a muffling is achieved by cross-sectional constrictions and deflections provided in the flow duct, for example, a spiral muffler, cannot, however, be optimized in terms of a maximum muffling, because both cross-sectional contractions and deflections lead to an increase in the flow resistance and hence to an undesired reduction of the pneumatic performance capacity. By contrast, large flow cross sections guarantee a low fluidic resistance and hence a high performance capacity. The configuration of an inlet muffler therefore always requires a compromise between a minimization of the sound emissions and the pneumatic performance capacity. A theoretically optimal muffler would be characterized in that the flow cross section likewise has a maximum at a maximum volume flow of the air or gas stream being delivered by the compressor, becoming lower with increasing throttling of the compressor and closing the inlet completely in case of complete throttling, in which case the volume flow thus drops to zero.

According to a special variant of the present invention, the above-described functionality is achieved at least approximately by an inlet muffler having at least one automatically closing valve element, which opens and closes as a function of the pressure difference present at the valve. The actuation of the valve takes place here preferably on the basis of the pressure difference present at the valve disk. The valve element is therefore advantageously configured in the form of a nonreturn valve, which reliably prevents the backflow of air and/or gas from the flow duct of the compressor impeller. The valve element preferably has a valve disk, which is configured in the form of a valve membrane.

A desired opening characteristic is set in another special embodiment by the rigidity of a valve membrane used as a valve disk, an arrangement of a valve membrane and/or a fastening of a valve membrane being selected as needed.

The valve element of an inlet muffler is preferably configured such that it releases a maximum flow cross section between a valve disk and a valve seat at maximum volume flow, i.e., at maximum pneumatic performance of the compressor, and a minimal flow cross section during maximally throttled operation of the compressor. As a result, a maximum possible minimization of the sound emitted through the inlet and hence maximum muffling is achieved during the operation.

Provisions are made in this connection according to a very special variant for a plurality of such valve elements with different opening characteristics to be connected in series, so that the characteristic of the compressor can be optimized as needed, for example, a constant compression is achieved over a predefined volume flow range.

At least one of the above-described valve elements may advantageously be used alone or together with a spiral muffler, which is configured according to one of the above-described embodiments, to minimize the sound released via the inlet, especially in order to prevent or at least reduce sound emissions that would be generated by the compressor impeller and would be released via the inlet against the flow direction of the air and/or gas stream being delivered. These sound emissions via the inlet usually become more intense if the compressor impeller is throttled at a constant speed level. It follows from this that the sound emission assumes a maximum value at an operating point at which there is no flow through the compressor.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
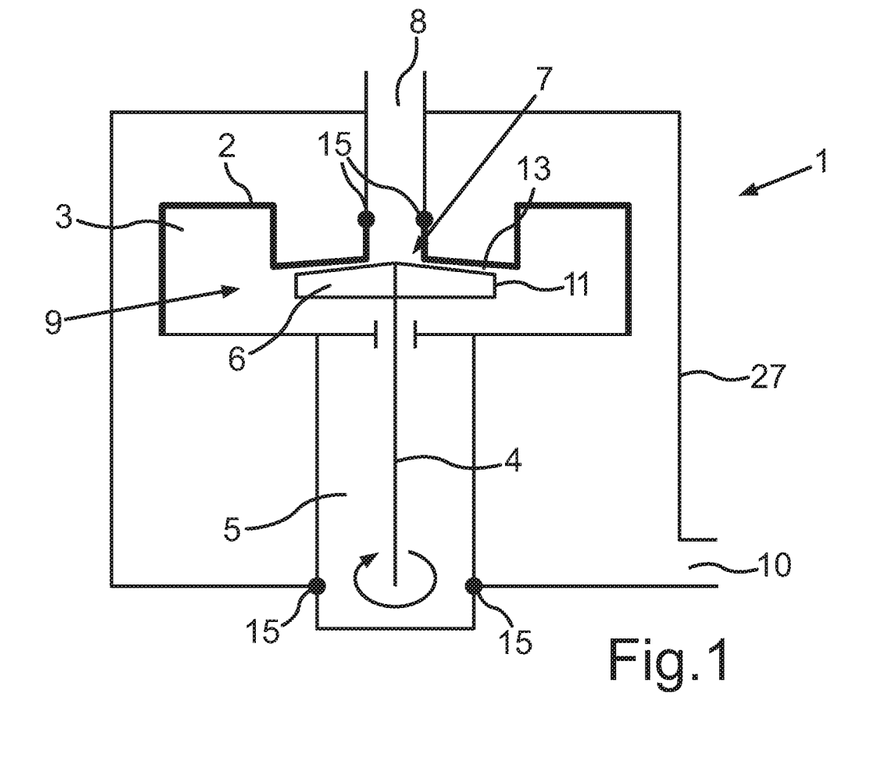
FIG. 1 is a schematic sectional view of a compressor known from the state of the art with primary housing and secondary housing.

Referring to the drawings, FIG. 1 shows first a compressor 1 for a ventilator or anesthesia device, as it is known from the state of the art. The compressor 1 has an electric motor 5, which drives a compressor impeller 6 via a drive shaft 4 as a function of the performance parameters necessary for ventilating a patient. The compressor impeller is mounted rotatably in an inner collection housing 2, which is configured as a spiral housing and which may also be called a primary housing, and into which housing air enters through a central inlet 8 during the operation. The compressor impeller 6 is configured as a radial compressor impeller, which is driven directly by the electric motor 5 as a function of the needed pneumatic performance. Air is drawn in during the operation via a central inlet 8, it is distributed radially outwards by the rotation of the compressor impeller 6, collected in the spiral collection housing 2 and delivered to the outlet 10. In order to maintain sound emissions as low as possible during the operation, the compressor is enclosed by a second housing 27, the so-called secondary housing, which likewise has an inlet as well as an outlet for the air and/or gas stream to be delivered. In order to prevent the transmission of vibrations, the unit comprising the electric motor 5, the compressor impeller 6 and the primary housing 2 is mounted with flexible, soft uncoupling elements 15 in the secondary housing 27. Therefore, the additional housing in the form of the secondary housing 27 is necessary above all because the connections between the electric motor 5 and the compressor impeller 6 as well as between the electric motor 5 and the primary housing 2 have a rigid configuration, so that vibrations, which are generated due to the operation above all at high motor speeds, are transmitted nearly undisturbed, depending on the configuration of the connection, to all housing parts connected thereto and are thus emitted into the surrounding area 16. Such a construction with two separate housings 2, 27 rules out a compact construction of a corresponding merit.

It can also be seen in FIG. 1 that the primary housing 2 encloses as a one-part collection housing the housing interior 3 with the compressor impeller 6 arranged therein. A small gap 13 is located now on the suction side 7 of the compressor impeller 6 between a cover area of the primary housing 2 and the compressor impeller 6. This gap 13 must be kept as small as possible in order to prevent or at least minimize a bypass flow from the delivery side 9 to the suction side 7, because this bypass flow reduces the performance capacity of the compressor. On the other hand, the gap 13 must be dimensioned such that a contact between the compressor impeller 6 and the cover area of the collection housing 2 is reliably prevented from developing in each operating state, especially also during an increase in the speed and/or a rise in the temperature of the compressor impeller 6. It follows directly from this that the contradiction between the requirements concerning a minimal height of the gap 13 between the cover area of the collection housing 2 and the compressor impeller 6 and the fixed position of the cover element of the collection housing, which is necessary for this, on the one hand, as well as the flexible suspension of a collection housing for guaranteeing the most effective muffling possible, on the other hand, represents a considerable structural problem.

Figure 2:
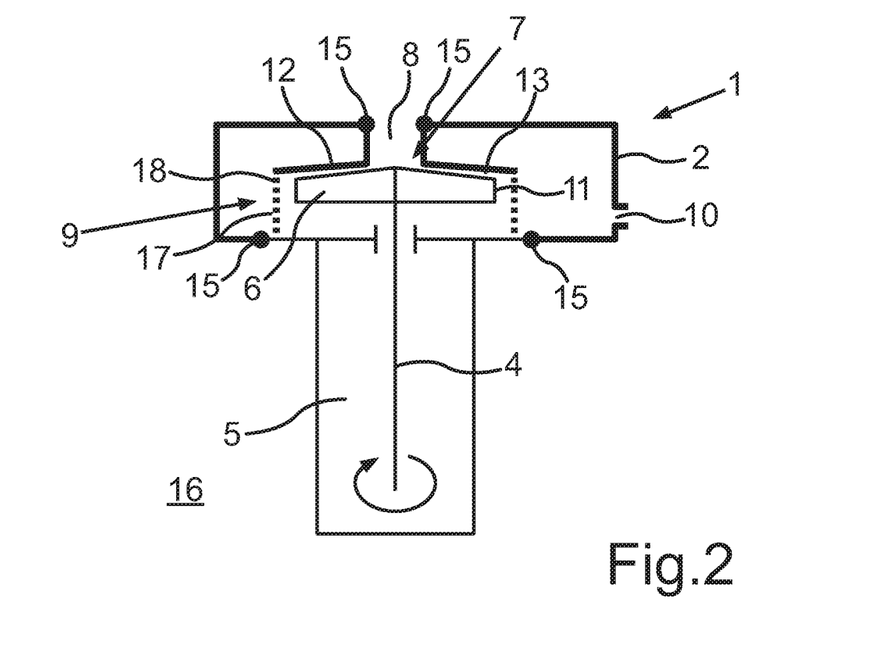
FIG. 2 is a schematic sectional view of a compressor configured according to the present invention.

FIG. 2 shows a compressor configured according to the present invention in a schematic sectional view. The compressor has a compressor impeller 6, which is mounted rotatably in a housing interior 3, and which is driven by an electric motor 5 via a drive shaft 4. The compressor impeller 6 is rotated by the electric motor 5 as a function of the needed air and/or gas stream, as a result of which the air and/or gas stream is delivered from the inlet 8 arranged upstream on a suction side 7 of the compressor impeller 6 through a flow duct 11 to an outlet 10 arranged downstream on the delivery side 9 of the compressor impeller 6. The housing interior 3 as well as the compressor impeller 6 arranged in it are enclosed by a spirally configured collection housing 2, which may therefore also be called a spiral housing, as well as by a disk-shaped cover element 12, wherein the cover element 12 defines the housing interior 3 especially on the suction side 7, and the collection housing 2 [defines] the housing interior 3 above all on the delivery side 9.

Consequently, the housing enclosing the housing interior 3 is thus formed according to the present invention from two parts, namely, from a spiral collection housing 2 and a disk-shaped cover element 12. In order to avoid the transmission of vibrations originating from the compressor impeller 6 and/or from the electric motor 5 to the collection housing 2, uncoupling elements 15 are arranged both between the cover element 12 and the collection housing 2 and between the collection housing 2 and a functional component 14, which is a part of the motor housing in this case. The housing enclosing the housing interior 3 with the compressor impeller 6 arranged therein has thus been split into two parts, namely, a cover element 12 above the compressor impeller 6 as well as the spiral collection housing 2, which can also be called spiral housing or volute.

According to the embodiment shown in FIG. 2, the cover element 12 has a disk-shaped configuration, and the inlet 8 for the air and/or gas stream is located centrally within the disk. The cover element 12 is connected on the inlet side via a flexible uncoupling element to the collection housing 2, so that a transmission of vibrations from the cover element 12 is reliably prevented or at least minimized. Furthermore, sealing of the housing interior 3 against the surrounding area is ensured by means of the uncoupling element 15 provided in this area.

On the side of the cover element 12 that faces away from the inlet 8, this [cover element 12] is supported on a flow guide unit 17. The flow guide unit 17 is supported, in turn, on a side facing away from the cover element 12 indirectly or directly on a functional component 14, for example, on a housing component of the electric motor 5. It is ensured in this manner that the cover element 12 is, on the one hand, uncoupled in respect to vibrations against the collection housing 2 by means of the uncoupling element 15 and, on the other hand, there is a rigid connection to the functional component 14, so that a comparatively small gap 13 can be obtained between the cover element 12 and the compressor impeller 6, without the risk of contacts being present during the operation.

The flow guide unit 17, on which the cover element 12 is supported, is arranged according to the embodiment shown in FIG. 2 on the delivery side of the compressor impeller 6, so that the air and/or gas stream leaving the compressor impeller 6 reaches the flow guide unit 17 and is deflected by this at least partially. The flow guide unit 17 shown has stationary guide blades 18, which do not adjoin directly the compressor impeller 6 rotating during the operation. The area between the compressor impeller 6 and the guide blades 18 is configured for the most frequently used operating range of the compressor in the form of a diffusor.

As can clearly be seen in the schematic view in FIG. 2, separation points between the cover element 12 and the collection housing 2, as well as between the collection housing 2 and the functional component 14, which forms a part of the motor housing here, are connected via uncoupling elements 15, which ensure, on the one hand, an uncoupling of the components adjoining on both sides in terms of vibrations, on the one hand, and seal the housing interior 3, to which pressure is admitted, against the surrounding area 16, on the other hand. Vibrations, which are generated especially by the electric motor 5, are not transmitted due to the uncoupling provided to the collection housing 2 directly defining the housing interior 3, or the vibration transmission is at least reduced considerably. According to the exemplary embodiment of the present invention, which is shown in FIG. 2, the collection housing 2 assumes the function that is assumed in the technical solutions known from the state of the art by the secondary housing 27 provided as an additional housing, as this is shown in FIG. 1. Based on the provision of the technical solution according to the present invention, it is possible to provide a compressor with comparatively small dimensions, whose pneumatic performance can even be increased compared to prior-art solutions in case of suitable dimensioning and configuration of the guide blades 18 and of the diffusor for a selected operating range.

Figure 3:
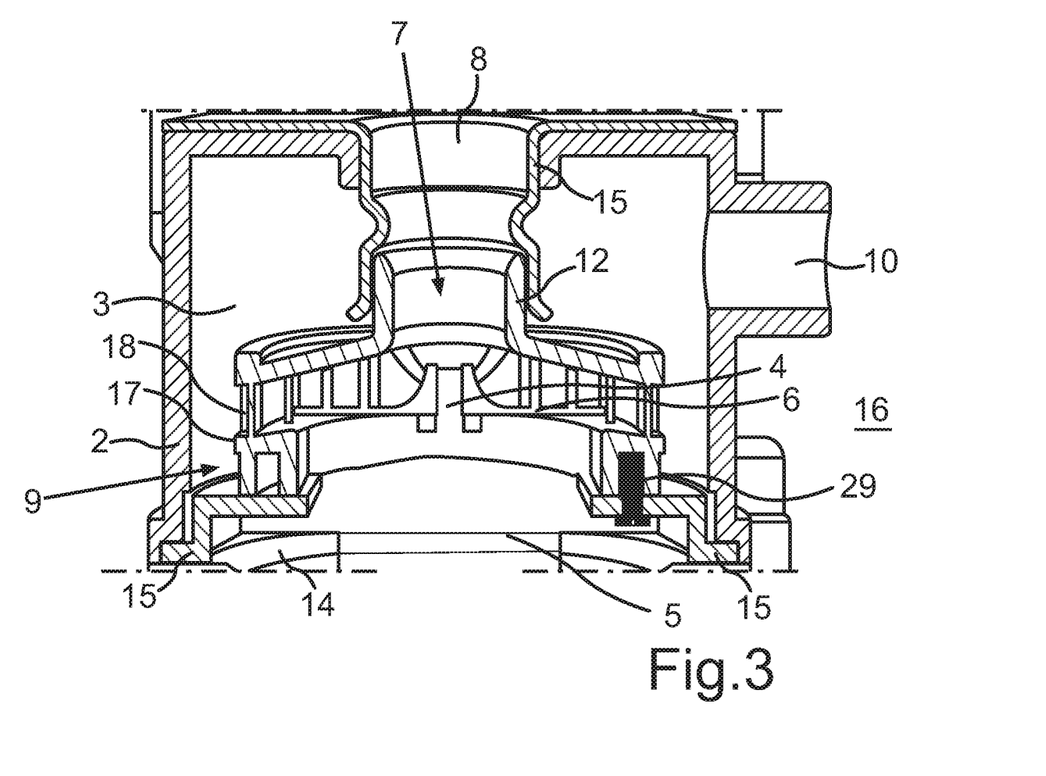
FIG. 3 is a sectional view of a compressor configured according to the present invention.

FIG. 3 shows a sectional view of a compressor configured according to the present invention with a spiral collection housing 2, with a cover element 12 and with uncoupling elements 15. The rotatably driven compressor impeller 6, which is driven by an electric motor 5 via a drive shaft 4, is arranged in the housing interior 3.

It is, in turn, essential for the present invention that the housing for the housing interior 3 as well as the compressor impeller 6 mounted rotatably therein is formed from the collection housing 2 as well as from a cover element 12. Uncoupling elements 15, which guarantee an uncoupling of the respective components adjoining the uncoupling element 15 in terms of vibrations, on the one hand, and a sealing of the housing interior 3, to which pressure is admitted, against the surrounding area 16, on the other hand, are provided both between the collection housing 2 and the cover element 12 and between the collection housing 2 and a functional component 14. The uncoupling element 15 arranged on the motor side is configured such that a vibration uncoupling is also brought about at a separation point between the collection housing 2 and a functional component 14, here a part of the housing of the electric motor 5. It is thus reliably ensured by this uncoupling element 15 that vibrations generated by the compressor impeller 6 and especially by the electric motor 5 are not transmitted to the collection housing 2 enclosing the housing interior 3 or are transmitted only slightly. The emission of disturbing sound is thus reliably avoided or at least considerably reduced. The flow guide unit 17 is connected on the motor side to the functional component 14 at least indirectly via at least one screw 29. This screw 29 advantageously assumes the function of an adjusting screw, so that the width of the gap 13 between the cover element 12 and the flow guide unit 17 can be set by suitably tightening and/or loosening the screw 29.

In addition, an inlet 8, through which an air and/or gas stream flows in the direction of the compressor impeller 6 during the rotation of a compressor impeller 6 arranged in the housing interior 3, is provided on the suction side 7 in the assembly unit shown in FIG. 3. During the rotation of the compressor impeller 6, this drawn-in air and/or gas stream is finally pushed by the compressor impeller 6 radially to the outside and is guided radially outwards in the direction of the wall of the collection housing 2 by the guide blades 18 of the flow guide element 17, which is connected to the cover element 12, or is alternatively configured in one piece with this. The compressed air and/or gas stream then leaves the collection housing 2 of the compressor through an outlet 10 and is fed, for example, to a mechanically ventilated patient.

The cover element provided on the suction side has a disk-shaped configuration and the inlet 8 is located centrally in the center of the disk. The cover element 12 is supported via the flow guide unit 17 downwards on the functional component 14, which is a housing part of the electric motor 5 in this case. An uncoupling element 15 is provided in the area of the inlet 8 at the separation point between the cover element 12 and the collection housing 2. This uncoupling element 15 ensures, on the one hand, that vibrations are not transmitted to the collection housing 2 and, on the other hand, it guarantees sealing of the pressurized housing interior 3 against the surrounding area 16.

Figure 4:
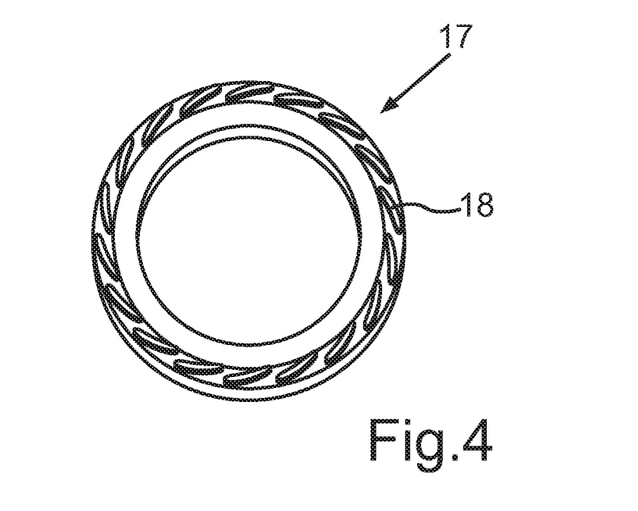
FIG. 4 is a sectional view of a flow guide unit of a compressor configured according to the present invention.

The flow guide unit 17 has on the delivery side 9 a plurality of guide blades 18, which are distributed radially over the circumference and which deflect the air and/or gas stream pushed radially outwards by the compressor impeller 6 in a suitable manner. The area between the delivery side of the compressor impeller 6 and the guide blades 18 is configured as a diffusor for an operating range, which frequently occurs. FIG. 4 shows in a perspective sectional view such a special flow guide unit 17, which has a ring-shaped configuration and has a plurality of guide blades 18 distributed over the outer circumference. The sectional plane extends here horizontally through the flow guide unit 17. The flow guide unit 17 shown is configured such that the cover element 12 provided according to the present invention can be supported on it. The flow guide unit 17 has for this purpose a suitable contact contour or may, as an alternative, be made in one piece with the cover element 12. In any case, the flow guide element 17 establishes the indirect or direct connection between the cover element 12 and the functional component 14 arranged on the motor side.

Figure 5:
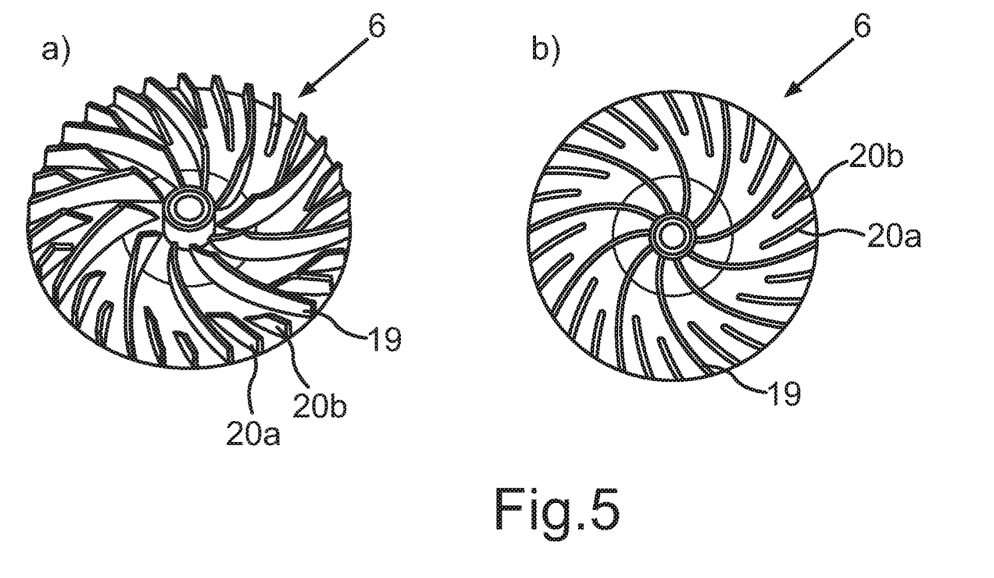
FIG. 5 is a perspective view as well as a top view of a compressor impeller of a compressor configured according to the present invention.

FIG. 5 shows in a perspective view a) as well as in a top view b) a specially configured compressor impeller 6, as it can advantageously be used for a compressor configured according to the present invention. An air and/or gas stream is delivered radially to the outside by means of the blades 19, 20 during the rotation of this compressor impeller 6. The compressor impeller 6 shown has first main blades 19, which extend at least almost completely from an outer circumference of the compressor impeller to the center of the compressor impeller, where this [compressor impeller] can be fastened to the drive shaft of an electric motor. According to the exemplary embodiment shown in FIG. 5, the compressor impeller 6 has 10 main blades 19. According to the embodiment shown in FIG. 5, two intermediate blades 20 each, which have different lengths, are arranged between the main blades 19, wherein the longer intermediate blades 20a are associated with the suction side and the shorter intermediate blades 20b are associated with the delivery side of the compressor in the mounted state. The longer intermediate blades 20a in the exemplary embodiment described have a length that is about 40% of the length of the main blades 19, while the length of the shorter intermediate blades 20b equals only about 30% of the length of the main blades 19. Based on such a configuration of the intermediate blades 20, swirling is advantageously prevented between the main blades 19 or is at least greatly minimized, so that the sound emissions otherwise caused hereby are likewise at least reduced.

The compressor impeller shown in FIG. 5 preferably has an outer diameter of 30 mm to 32 mm. Further, it is advantageous if 9 to 13 main blades 19 are provided, between which, as was explained above, two differently dimensioned intermediate blades 20 each are arranged.

It is advantageous if the maximum height of the main blades 19 has a value between 5 mm and 6 mm and the top edge of the main blades 19 is sloped in the direction of direction of the outer circumference of the compressor impeller 6 in at least some sections. An angle between 75° and 80° appears to be useful here. What is essential for the effective operation of a compressor impeller 6 is above all the configuration of the blade duct. According to the embodiment shown, the dimensions are selected to be such that the outlet cross section is about 30% larger than the inlet cross section.

Figure 6:
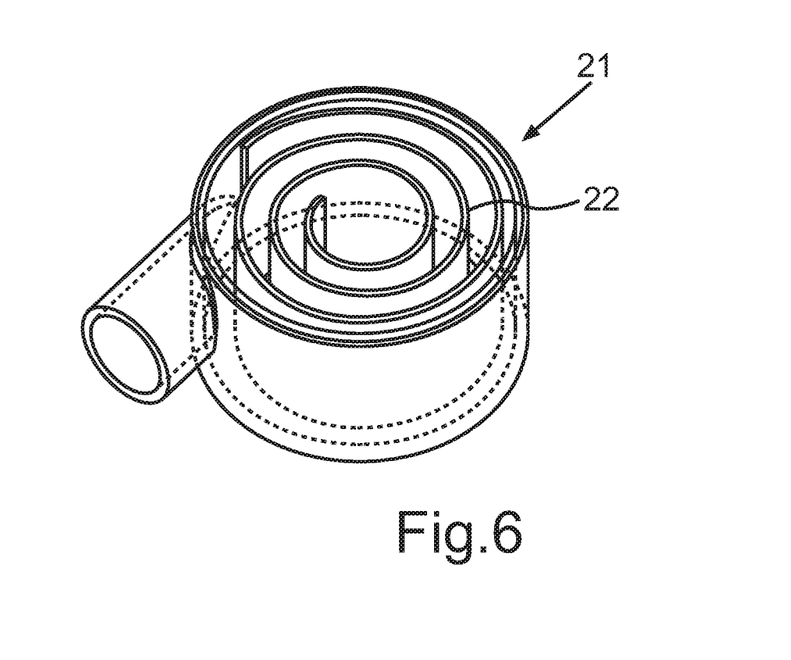
FIG. 6 is a perspective view of an inlet muffler configured as a spiral muffler with a partial spiral.
Figure 7:
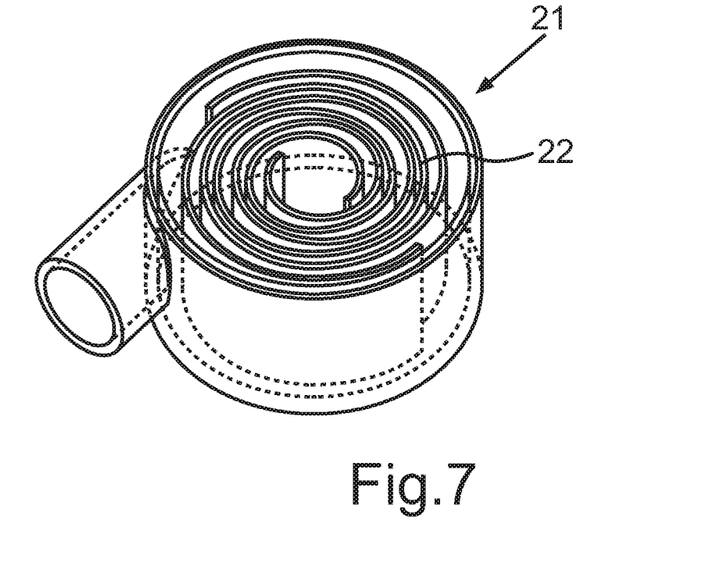
FIG. 7 is a perspective view of an inlet muffler configured as a spiral muffler with two partial spirals interlaced one in the other.

FIG. 6 shows an inlet muffler 21 configured as a spiral muffler with a spiral element 22 arranged therein. Due to the reduction of the flow cross section in the interior of the inlet muffler 21 as well as the deflection of the flow, the sound emissions emitted in the direction of the inlet of the inlet muffler 21 are minimized. The flow cross section of the inlet muffler 21 is dimensioned such that it is about 30% larger than the inlet cross section of the compressor. If the distance between the individual turns of the spiral element 22 is kept short, the emission of the flow noises emitted backwards via the inlet of a compressor can be minimized. Depending on the respective necessary pneumatic performance of a compressor, the excessive reduction of the flow cross section in the inlet muffler does, however, have a considerable disadvantage. In order to ensure a defined flow cross section despite a reduced wall clearance in the spiral element 22, it would thus be necessary to increase the resulting overall height of an inlet muffler 21, so that this would rapidly become comparatively great. To obtain a compact and flat structural shape of an inlet muffler, the spiral element 22 provided in the interior can therefore preferably be split, as is shown in FIG. 7, into two partial spirals, which are interlaced in one another. The spiral element shown in FIG. 7, which comprises two partial spirals, has the same flow cross section as the one shown in FIG. 6. However, the wall clearance was reduced by half, so that the muffling characteristic for flow noises emitted via the inlet is markedly improved with similar external dimensions of the inlet muffler 21.

An inlet muffler 21, in which a muffling is achieved by cross section contractions and deflections provided in the flow duct, for example, a spiral muffler as it is shown in FIGS. 6 and 7, cannot, however, be optimized in respect of a maximum muffling, because both cross-sectional contractions, increases in the length of the flow duct as well as deflections lead to an increase in the flow resistance and hence to an undesired reduction of the pneumatic performance capacity. By contrast, large flow cross sections and short flow ducts guarantee a low fluidic resistance and hence a high performance capacity. The configuration of an inlet muffler therefore always requires a compromise between a minimization of the sound emissions and the pneumatic performance capacity. A theoretically optimal muffler would be characterized in that the flow cross section likewise has its maximum in case of a maximum volume flow of the air or gas stream being delivered by the compressor, becoming smaller with increasing throttling of the compressor and closing the inlet completely in case of full throttling, when the volume flow thus assumes zero value.

A special possibility for configuring an inlet muffler 21 for a compressor configured according to the present invention will therefore be explained in connection with FIG. 8. The above-described functionality is achieved here at least approximately by an inlet muffler 21 having at least one automatically closing valve element 23, which opens and closes as a function of the pressure differences present at the valve. The valve element 23 is preferably actuated here based on the pressure difference present at the valve disk 24. The valve element 23 is advantageously configured therefore in the form of a nonreturn valve, which reliably prevents the backflow of air and/or gas from the flow duct of the compressor impeller 6. The valve element shown in FIG. 8 has a valve disk 24, which has a valve membrane 28. The necessary opening characteristic is set by the stiffness of the valve membrane 28 used, as the well as the shape and the arrangement of said valve membrane in the flow duct and/or its fastening of a valve membrane are selected as needed.

The shown valve element 24 of an inlet muffler 21 is configured such that it releases a maximum valve opening 26 for a maximum flow cross section between the valve disk 24 and the valve seat 25 at maximum volume flow, i.e., at maximum pneumatic performance of the compressor, and for a minimal valve opening 26 for a minimal flow cross section during maximally throttled operation of the compressor. Maximum possible minimization of the sound emitted through the inlet and hence maximum muffling are achieved hereby during the operation.

Figure 8:
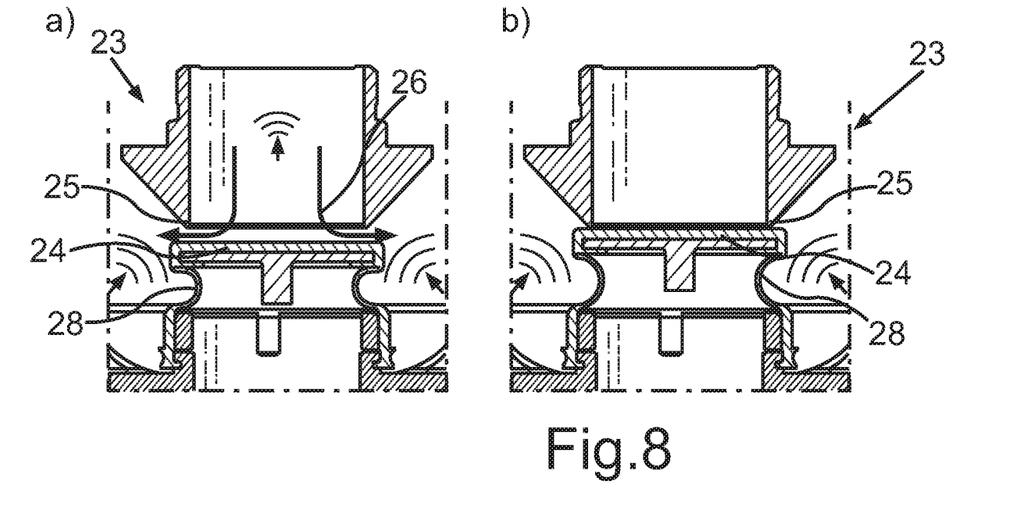
FIG. 8 is a sectional view of an inlet muffler with a nonreturn valve in the open and closed operating positions.

FIG. 8 a) shows in this connection an operating state in which the valve element 23 is opened and the valve disk 24 is lifted off from the valve seat 25, so that the valve opening 26 is released at least partially. By contrast, FIG. 8 b) shows an operating state in which the valve element 24 is closed and the valve disk 25 is in contact along its circumference with the valve seat 26. It is conceivable, in principle, to provide in an inlet muffler 21 a valve element 24, as it was described above, or to use at least two such valve elements. If a plurality of such valve elements 24 with different opening characteristics are connected in series, the characteristic of the compressor can be optimized as needed, so that, for example, a constant compression can be achieved over a predefined range of volume flows.

Likewise, at least one of the above-described valve elements 24 may be used alone or together with a spiral muffler, as it is shown in FIGS. 6 and 7, to minimize the sound released via the inlet 7, especially in order to prevent or at least reduce sound emissions, which would be generated by the compressor impeller 6 and would be released via the inlet 8 against the flow direction of the air and/or gas stream being delivered. These sound emissions via the inlet 8 usually become more intense if the compressor impeller 6 is throttled at a constant speed level. It follows from this that the sound emission assumes a maximum at an operating point at which there is no flow through the compressor.

While specific embodiments of the invention have been shown and described in detail to illustrate the application of the principles of the invention, it will be understood that the invention may be embodied otherwise without departing from such principles.

LIST OF REFERENCE NUMBERS

1 Compressor
2 Collection house
3 Housing interior
4 Drive shaft
5 Electric motor
6 Compressor impeller
7 Suction side
8 Inlet
9 Delivery side
10 Outlet
11 Flow duct
12 Cover element
13 Gap
14 Functional component
15 Uncoupling element
16 Surrounding area
17 Flow guide unit
18 Guide blade
19 Main blade
20 Intermediate blade
20a longer intermediate blade
20b shorter intermediate blade
21 Inlet muffler
22 Spiral element
23 Valve element
24 Valve disk
25 Valve seat
26 Valve opening
27 Secondary housing
28 Valve membrane
29 Screw

The invention claimed is:

1. A compressor for delivering an air and/or gas stream, the compressor comprising:
a housing, with a housing interior;
a rotatably mounted compressor impeller in the housing interior;
an electric motor;
a drive shaft, the compressor impeller being connected to the electric motor via the drive shaft, during the rotation of which the air and/or gas stream is delivered from an inlet arranged upstream on a suction side of the compressor impeller through a flow duct to an outlet arranged downstream on a delivery side of the compressor impeller;
a cover element, wherein the compressor impeller, arranged in the housing interior, is enclosed in at least some areas by the housing, which is configured as a collection housing for the air and/or gas stream leaving the compressor impeller and is arranged at least partially on the delivery side of the compressor impeller, and by the cover element, which is arranged at least partially on the suction side of the compressor impeller and is separated in at least some sections from the compressor impeller by a gap, the collection housing having a shape of a spiral;
a functional component connected at least indirectly to the compressor impeller and/or to the electric motor; and
an uncoupling element arrangement comprising at least one respective uncoupling element, the uncoupling element arrangement being arranged between the cover element and the collection housing and between the functional component and the collection housing for vibration damping and for at least partial sealing of the housing interior against a surrounding area.

2. A compressor in accordance with claim 1, wherein the functional component is a part of the housing or another housing and/or is a part of an encapsulation of the electric motor and/or is connected indirectly or directly to the electric motor.

3. A compressor in accordance with claim 1, wherein the cover element is configured in the form of a disk, which has a passage for the air and/or gas stream in an interior of the disk.

4. A compressor in accordance with claim 1, further comprising a flow guide unit, wherein the cover element is connected in at least some areas indirectly or directly to the flow guide unit, which has at least one guide blade for guiding the air and/or gas stream released on the delivery side of the compressor impeller.

5. A compressor in accordance with claim 4, wherein:
the flow guide unit has a ring-shaped configuration and at least another guide blade to provide a plurality of guide blades arranged on a ring surface; and
the compressor impeller is arranged in an interior of the flow guide unit, such that the air and/or gas stream released from the compressor impeller on the delivery side at least partially reaches the plurality of guide blades.

6. A compressor in accordance with claim 1, wherein the compressor impeller comprises main blades extending in a radial direction from an outer circumference of the compressor impeller at right angles at least over an entire cross section of the flow duct and at least two respective intermediate blades arranged between the main blades and having a shorter configuration than the main blades.

7. A compressor in accordance with claim 6, wherein the intermediate blades, arranged between two main blades, have different lengths in the radial direction, have unequal profiles and/or have blade surface areas.

8. A compressor in accordance with claim 1, further comprising at least one inlet muffler arranged upstream of the compressor impeller.

9. A compressor in accordance with claim 8, wherein the inlet muffler is configured as a spiral muffler.

10. A compressor in accordance with claim 8, wherein the inlet muffler is configured as a spiral muffler with at least two separate spiral elements arranged at least partially in one another.

11. A compressor in accordance with claim 1, further comprising at least one valve element, opening, on the basis of a pressure difference caused by rotation of the compressor impeller in the flow direction of the air and/or gas stream, arranged upstream of the compressor impeller.

12. A compressor in accordance with claim 11, wherein the valve element comprises a movably mounted valve membrane.

13. A ventilator or anesthesia device comprising a compressor, the compressor comprising:
a housing, with a housing interior;
a rotatably mounted compressor impeller in the housing interior;
an electric motor;
a drive shaft, the compressor impeller being connected to the electric motor via the drive shaft, during the rotation of which the air and/or gas stream is delivered from an inlet arranged upstream on a suction side of the compressor impeller through a flow duct to an outlet arranged downstream on a delivery side of the compressor impeller;
a cover element, wherein the compressor impeller, arranged in the housing interior, is enclosed in at least some areas by the housing, which is configured as a collection housing for the air and/or gas stream leaving the compressor impeller and is arranged at least partially on the delivery side of the compressor impeller, and by the cover element, which is arranged at least partially on the suction side of the compressor impeller and is separated in at least some sections from the compressor impeller by a gap, the collection housing having a shape of a spiral;
a functional component connected at least indirectly to the compressor impeller and/or to the electric motor; and
an uncoupling element arrangement comprising at least one respective uncoupling element, the uncoupling element arrangement being arranged between the cover element and the collection housing and between the functional component and the collection housing for vibration damping and for at least partial sealing of the housing interior against a surrounding area.

14. A ventilator or anesthesia device in accordance with claim 13, wherein the functional component is a part of the housing or another housing and/or is a part of an encapsulation of the electric motor and/or is connected indirectly or directly to the electric motor.

15. A ventilator or anesthesia device in accordance with claim 13, wherein the cover element is configured in the form of a disk, which has a passage for the air and/or gas stream in an interior of the disk.

16. A ventilator or anesthesia device in accordance with claim 13, further comprising a flow guide unit, wherein the cover element is connected in at least some areas indirectly or directly to the flow guide unit, which has at least one guide blade for guiding the air and/or gas stream released on the delivery side of the compressor impeller.

17. A ventilator or anesthesia device in accordance with claim 13, wherein:
the flow guide unit has a ring-shaped configuration and at least another guide blade to provide a plurality of guide blades arranged on a ring surface; and
the compressor impeller is arranged in a interior of the flow guide unit such that the air and/or gas stream released from the compressor impeller on the delivery side reaches at least partially the plurality of guide blades.

18. A ventilator or anesthesia device in accordance with claim 13, wherein the compressor impeller comprising main blades extending in a radial direction from an outer circumference of the compressor impeller at right angles at least over an entire cross section of the flow duct and at least two respective intermediate blades arranged between the main blades and having a shorter configuration than the main blades.

19. A ventilator or anesthesia device in accordance with claim 13, further comprising at least one inlet muffler arranged upstream of the compressor impeller wherein the inlet muffler is configured as a spiral muffler.

20. A ventilator or anesthesia device in accordance with claim 13, further comprising at least one valve element, opening, on the basis of a pressure difference caused by rotation of the compressor impeller in the flow direction of the air and/or gas stream, arranged upstream of the compressor impeller.

* * * * *